US012673133B2

(12) United States Patent
Lee et al.

(10) Patent No.: US 12,673,133 B2
(45) Date of Patent: Jul. 7, 2026

(54) BIODEGRADABLE POLYMER FINE PARTICLE FOR FILLER, FREEZE-DRIED BODY INCLUDING THE SAME, MANUFACTURING METHOD THEREOF, AND FILLER INJECTION INCLUDING FREEZE-DRIED BODY

(71) Applicant: ULTRA V CO., LTD., Incheon (KR)

(72) Inventors: Cheong Cheon Lee, Seoul (KR); Lia Priscilla, Seoul (KR); Min Seok Kwak, Seoul (KR); Jung Woo Han, Seoul (KR); Jung Ryul Ham, Paju-si (KR); Han Jin Kwon, Seoul (KR)

(73) Assignee: ULTRA V CO., LTD., Incheon (KR)

( * ) Notice: Subject to any disclaimer, the term of this patent is extended or adjusted under 35 U.S.C. 154(b) by 0 days.

(21) Appl. No.: 18/414,411

(22) Filed: Jan. 16, 2024

(65) Prior Publication Data

US 2024/0157025 A1 May 16, 2024

Related U.S. Application Data

(62) Division of application No. 17/582,897, filed on Jan. 24, 2022, now abandoned.

(30) Foreign Application Priority Data

Jan. 25, 2021 (KR) ........................ 10-2021-0010204

(51) Int. Cl.
| | |
|---|---|
| *A61L 27/44* | (2006.01) |
| *A61L 27/18* | (2006.01) |
| *A61L 27/20* | (2006.01) |
| *A61L 27/58* | (2006.01) |

(52) U.S. Cl.
CPC .............. *A61L 27/18* (2013.01); *A61L 27/20* (2013.01); *A61L 27/44* (2013.01); *A61L 27/58* (2013.01); *A61L 2300/60* (2013.01); *A61L 2400/06* (2013.01); *A61L 2430/34* (2013.01)

(58) Field of Classification Search
CPC ............. A61L 2300/60; A61L 2400/06; A61L 2400/18; A61L 2430/34; A61L 27/18; A61L 27/20; A61L 27/44; A61L 27/48; A61L 27/56; A61L 27/58; C08L 1/26; C08L 67/04
See application file for complete search history.

(56) References Cited

U.S. PATENT DOCUMENTS

| | | | | |
|---|---|---|---|---|
| 5,434,146 A | * | 7/1995 | Labrie ................... | A61K 31/575 514/169 |
| 6,424,091 B1 | * | 7/2002 | Sawada ............. | H01J 37/32541 315/111.21 |
| 6,716,251 B1 | | 4/2004 | Asius | |
| 9,982,090 B2 | | 5/2018 | Choi | |
| 2018/0311333 A1 | * | 11/2018 | Ruegg ..................... | A61P 27/02 |

FOREIGN PATENT DOCUMENTS

| | | | |
|---|---|---|---|
| CN | 110339397 | A | 10/2019 |
| JP | 2010-505819 | A | 2/2010 |
| JP | 2015-533521 | A | 11/2015 |
| JP | 2018-512959 | A | 5/2018 |
| JP | 2019-516524 | A | 6/2019 |
| KR | 10-2009-0108874 | A | 10/2009 |
| KR | 10-2016-039006 | A | 4/2016 |
| KR | 10-1942449 | B1 | 1/2019 |
| KR | 10-2051044 | B1 | 12/2019 |
| KR | 10-2089560 | B1 | 3/2020 |
| KR | 10-2193951 | B1 | 12/2020 |
| WO | 2017/163072 | A1 | 9/2017 |

OTHER PUBLICATIONS

CN110339397, machine translation, Oct. 18, 2019, pp. 1-9 (Year: 2019).*

Wan, Yuqing, et al., Biomaterials 25 (2004) 4777-4783 (Year: 2004).*

Abdul-Fattah, Ahmad M., Journal of Pharmaceutical Sciences, vol. 96, No. 8, Aug. 2007, pp. 1983-2008 (Year: 2007).*

JP2005166458, machine translation, (2005), pp. 1-11 (Year: 2005).*

An Office Action; "Grant of Patent," mailed by the Korean Intellectual Property Office on Apr. 15, 2021, which corresponds to Korean Patent Application No. 10-2021-0010204.

Abdulrahman Baki et al., Surface modification of PDLLGA microspheres with gelatine methacrylate: Evaluation of adsorption, entrapment, and oxygen plasma treatment approaches, Acta Biomaterialia, vol. 53, Jan. 12, 2017, p. 450-459.

The extended European search report issued by the European Patent Office on Jun. 24, 2022, which corresponds to European Patent Application No. 22153146.0-1109 and is related to Korean Patent Application No. 10-2021-0010204.

An Office Action; "Notice of Reasons for Refusal," mailed by the Japanese Patent Office on Mar. 22, 2023, which corresponds to Japanese Patent Application No. 2022-008425 and is related to U.S. Appl. No. 18/414,411.

* cited by examiner

*Primary Examiner* — Brian-Yong S Kwon
*Assistant Examiner* — Lyndsey M Beckhardt
(74) *Attorney, Agent, or Firm* — Studebaker Brackett PLLC

(57) ABSTRACT

Disclosed herein are a biodegradable polymer microparticle for a filler, a freeze-dried body including the same, a manufacturing method thereof, and filler injection including the freeze-dried body. The freeze-dried body includes hydrophilic surface-treated biodegradable polymer microparticle and a biocompatible carrier, wherein the hydrophilic surface-treated biodegradable polymer microparticle has an average particle diameter ($D_{50}$) of 20 to 50 μm and is polydioxanone which has a carboxyl group on the surface thereof. The hydrophilic surface-treated biodegradable polymer microparticle is a plasma surface-treated product or a base surface-treated product using discharge of the biodegradable polymer microparticle. The content of the biocompatible carrier is 1 to 5 parts by weight based on 100 parts by weight of the freeze-dried body.

8 Claims, 5 Drawing Sheets

FIG. 1

| Sample | Time | | |
|---|---|---|---|
| | 0 min | 15 min | 60 min |
| Example 1 | | | |
| Comparative Example 1 | | | |
| Comparative Example 2 | | | |

FIG. 2

| Sample | Time | | |
| --- | --- | --- | --- |
| | 0 min | 15 min | 60 min |
| Example 2 | | | |
| Comparative Example 3 | | | |
| Comparative Example 6 | | | |

BIODEGRADABLE POLYMER FINE PARTICLE FOR FILLER, FREEZE-DRIED BODY INCLUDING THE SAME, MANUFACTURING METHOD THEREOF, AND FILLER INJECTION INCLUDING FREEZE-DRIED BODY

CROSS-REFERENCE TO RELATED APPLICATION

The present application is a divisional application of the U.S. patent application Ser. No. 17/582,897, filed on Jan. 24, 2022, which claims the benefit of priority to Korean Patent Application No. 10-2021-0010204, filed on Jan. 25, 2021, in the Korean Intellectual Property Office. The disclosures of the above-listed applications are hereby incorporated by reference herein in their entirety.

BACKGROUND

1. Technical Field

The present disclosure relates to a biodegradable polymer microparticle for a filler, a freeze-dried body including the same, a manufacturing method thereof, and filler injection including the freeze-dried body.

2. Description of Related Art

Biodegradable polymer microparticles are materials that recently begin to get spotlight as a material for tissue repair applicable to the face and the whole body. The biodegradable polymer does not contain components harmful to the human body unlike conventional hyaluronic acid hydrogel, and can be decomposed over a long time of 6 months to 4 years, thereby being applicable to various purposes like a filler.

A biodegradable polymer microparticle for a filler is manufactured to have an excipient containing natural polymers due to hydrophobicity of biodegradable polymers and low dispersibility. The excipient raises viscosity of injections to increase injection ability, and at the same time, lowers the degree of satisfaction of a procedure since being decomposed within several weeks after being injected into the human body and lowering the entire volume including the excipient. Therefore, a development of a new composition for a biodegradable polymer microparticle filler which does not use an excipient is required.

Korean Patent No. 10-1942449 discloses a filler composition in which 10 to 50% by weight of biodegradable polymer microparticles having a size of 10 to 200 μm are included, and the remainder excluding the polymer microparticles includes an excipient for maintaining dispersibility of the injection agent.

However, when the content of the excipient is less than 20%, the dispersibility of the biodegradable polymer microparticles is reduced.

Therefore, necessity for filler injection including biodegradable polymer microparticles, which have excellent dispersibility while reducing the content of the excipient, is increased.

SUMMARY

In an aspect of the present disclosure, it is an object to provide a freeze-dried body for a filler which has excellent dispersibility and is easily injected in a state in which the content of an excipient is reduced.

In another aspect of the present disclosure, it is another object to provide a method for manufacturing a freeze-dried body for a filler.

In a further aspect of the present disclosure, it is a further object to provide filler injection including the freeze-dried body for a filler.

In a still further aspect of the present disclosure, it is a further object to provide a new biodegradable polymer microparticle.

To accomplish the above objects, in an aspect of the present disclosure, there is provided a freeze-dried body for a filler comprising hydrophilic surface-treated biodegradable polymer microparticle and a biocompatible carrier, wherein the hydrophilic surface-treated biodegradable polymer microparticle has an average particle diameter ($D_{50}$) of 20 to 50 μm and is polydioxanone which has a carboxyl group on the surface thereof, wherein the hydrophilic surface-treated biodegradable polymer microparticle is a plasma surface-treated product or a base surface-treated product using discharge of the biodegradable polymer microparticle, wherein the content of the biocompatible carrier is 1 to 5 parts by weight based on 100 parts by weight of the freeze-dried body.

In another aspect of the present disclosure, there is provided a manufacturing method of a freeze-dried body for a filler comprising the operations of: preparing a biodegradable polymer microparticle for a filler having an average particle diameter of 20 to 50 λm; surface-treating the biodegradable polymer microparticle with plasma or base to manufacture a surface-treated biodegradable polymer microparticle; dissolving the hydrophilic surface-treated biodegradable polymer microparticle, the biocompatible carrier, and distilled water to obtain a mixed solution; and freeze-drying the mixed solution to obtain a freeze-dried body.

In a further aspect of the present disclosure, there is provided a filler injection includes: a freeze-dried body; and one or more selected from injection water, sterilized water, and distilled water.

In a still further aspect of the present disclosure, there is provided a biodegradable polymer microparticle for a filler which has an average particle diameter ($D_{50}$) of 20 to 100 μm, and is a hydrophilic surface-treated biodegradable polymer microparticle, wherein the hydrophilic surface-treated biodegradable polymer microparticle is a plasma surface-treated product or a base surface-treated product using discharge of the biodegradable polymer microparticle.

According to one aspect, biodegradable polymer microparticles for a filler and filler injection which has excellent dispersibility and is easily injected can be manufactured simply using uses reduced content of the excipient.

BRIEF DESCRIPTION OF THE DRAWINGS

FIG. 1 is a view illustrating precipitation evaluation results of a hydrophilic surface-treated biodegradable polymer microparticle according to an example 1 and a biodegradable polymer microparticle according to comparative examples 1 and 2.

FIG. 2 is a view illustrating precipitation evaluation results of a hydrophilic surface-treated biodegradable polymer microparticle according to an example 2 and a biodegradable polymer microparticle according to comparative examples 5 and 6.

DETAILED DESCRIPTION

Figure 3:
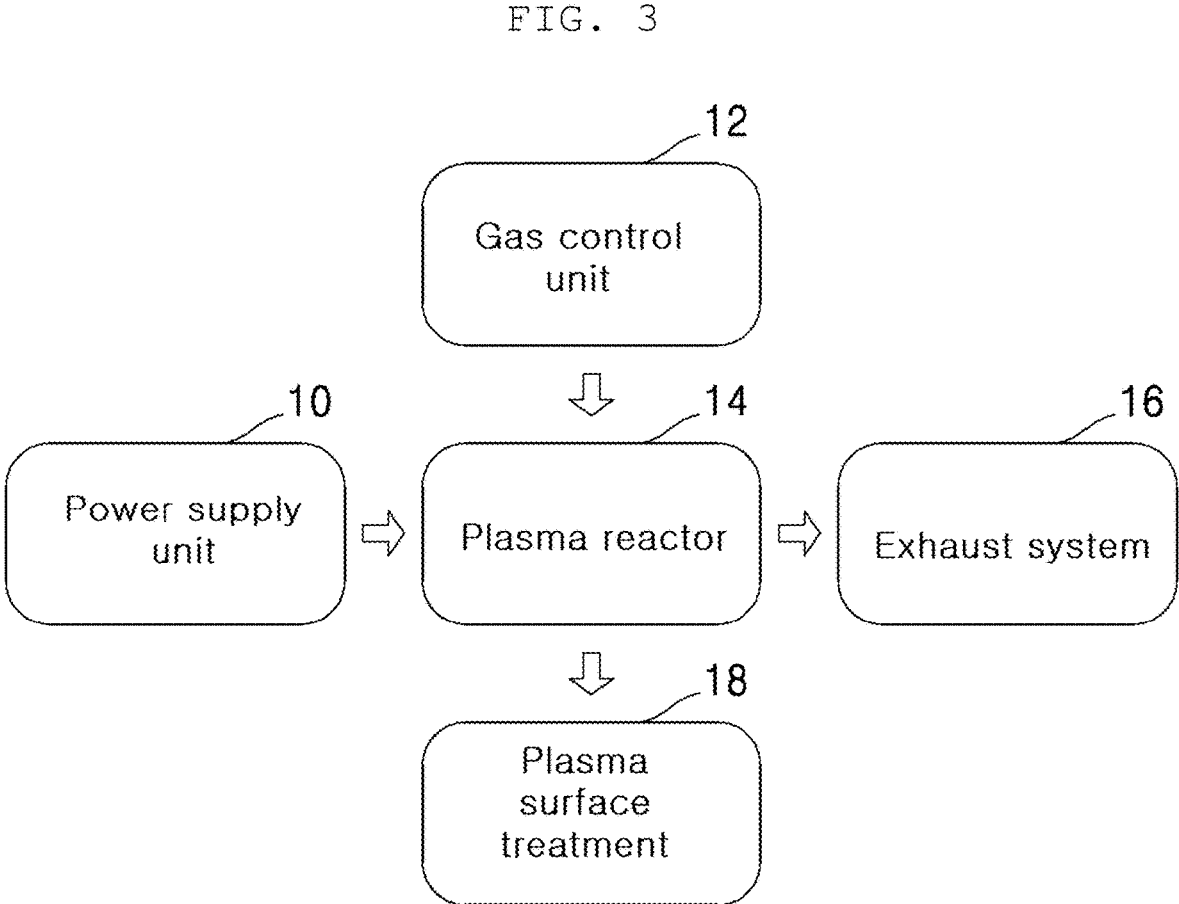
FIG. 3 is a block diagram of a plasma reaction device using electric discharge of a biodegradable polymer microparticle according to the present disclosure.

The present inventive concept described below can apply various transforms and may have various embodiments, and will be described in detail with reference to the drawings. However, this is not intended to limit the inventive concept to particular embodiments, and it is to be understood that all of changes, equivalents, or substitutes are included in the technical scope of the present inventive concept.

Additionally, in the attached drawings, dimensions of the components are more enlarged than they actually are in order to clarify the present disclosure. It will be understood that terms, such as "first" or "second" may be used in the specification to describe various components but are not restricted to the above terms. The terms may be used to discriminate one component from another component. For instance, the first component may be named as the second component, and on the contrary, the second component may be also named as the first component within the scope of the present disclosure. The singular form of the components may be understood into the plural form unless otherwise specifically stated in the context.

It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts. In addition, when a portion, such as a layer, a membrane, a region, a plate or the like, is "on" another portion, it includes a case that the portion is "directly on" another portion, as well as a case that a further portion exists between the portions. On the other hand, if a portion, such as a layer, a membrane, a region, and a plate is "under" another portion, it includes not only a case that the portion is "directly below" another portion but also a case that a further portion exists between the portions.

Hereinafter, a biodegradable polymer microparticle for a filler, filler injection including the same, and a manufacturing method thereof according to preferred embodiments of the present disclosure will be described in more detail.

The biodegradable polymer microparticle is a hydrophilic surface-treated biodegradable polymer microparticle having an average particle diameter ($D_{50}$) of 20 to 50 μm. The hydrophilic surface-treated biodegradable polymer microparticle for a filler is a biodegradable polymer microparticle which a plasma surface-treated product or a base surface-treated product using dielectric barrier discharge of the biodegradable polymer microparticle.

Moreover, the present disclosure provides a freeze-dried body for a filler including the hydrophilic surface-treated biodegradable polymer microparticle and a biocompatible carrier. An average particle diameter ($D_{50}$) of the hydrophilic surface-treated biodegradable polymer microparticle is 20 to 50 μm. The hydrophilic surface-treated biodegradable polymer microparticle is a plasma surface-treated product or a base surface-treated product using discharge of the biodegradable polymer microparticle, and the biocompatible carrier is 1 to 5 parts by weight based on 100 parts by weight of the freeze-dried body.

The biocompatible carrier is, for example, 1 to 4 parts by weight, 1 to 3 parts by weight, or 2 to 3 parts by weight based on 100 parts by weight of the freeze-dried body.

In the present specification, the biocompatible carrier means an excipient.

The biocompatible carrier can use one or more selected from alginic acid and its salt, hyaluronic acid and its salt, carboxymethyl cellulose, sodium carboxymethyl cellulose, dextran and its salt, collagen, gelatin, and elastin.

The plasma surface-treated product using discharge of the biodegradable polymer microparticle is a product obtained by applying voltage to a biodegradable polymer microparticle for a filler to induce discharge and perform discharge treatment of the biodegradable polymer microparticle.

The discharge treatment of the biodegradable polymer microparticle is carried out by injecting 400 to 600 mL/min of air in a plasma reaction device, applying 300 Hz to 500 Hz of alternating current to an electrode to which a power supply unit is connected to obtain plasma-treated air, and bringing the plasma-treated air into contact with the biodegradable polymer microparticle.

If the content of the biocompatible carrier is less than 1 part by weight, dispersibility of the freeze-dried body is deteriorated when filler injection is manufactured using the freeze-dried body containing the biodegradable polymer microparticle. Furthermore, if the content of the biocompatible carrier exceeds 1 part by weight, an injection force is increased due to an increase of viscosity of injections for a filler containing the freeze-dried body, and at the same time, the biocompatible carrier lowers the degree of satisfaction of the treatment since being decomposed within several weeks after being injected into the human body and lowering the entire volume including the excipient.

Additionally, the filler injection according to the present disclosure is at least one selected from a freeze-dried body for a filler, injection water, sterilized water, and distilled water, the average particle diameter ($D_{50}$) of the hydrophilic surface-treated biodegradable polymer microparticles for a filler is 20 to 50 μm, and the hydrophilic surface-treated biodegradable polymer microparticle is a plasma surface-treated product or a base surface-treated product using discharge.

In general, the biodegradable polymer microparticle filler essentially needs an excipient when injection is manufactured using the biodegradable polymer microparticles since having low dispersibility to distilled water due to hydrophobicity of the biodegradable polymers. The excipient is one of additives serving to make shapes of products when medicines are manufactured.

However, in order to maintain excellent dispersibility of the injection, if more than a predetermined content of the excipient is used, the viscosity of the injection must be increased to increase an injection force, and the entire volume including the excipient is reduced since the excipient is decomposed within several weeks after being injected into the human body, thereby lowering the degree of satisfaction of the treatment. Therefore, a biodegradable polymer microparticle filler having excellent dispersibility without using the excipient is required. Moreover, existing biodegradable polymer microparticles for a filler are deteriorated in dispersion stability due to self-aggregation of polymer particles as time goes by even if the biodegradable polymer filler maintains excellent dispersibility in distilled water.

The present disclosure completed a freeze-dried body and filler injection including the freeze-dried body, which can increase dispersibility by selecting a biodegradable polymer microparticle having an average particle diameter of 20 to 50 μm to control a particle size, use small excipients by performing surface-treatment of the biodegradable polymer microparticle with plasma or base using discharge to induce a hydrophilic group, and effectively prevent self-aggregation of the biodegradable polymer microparticle to greatly increase dispersion stability.

The freeze-dried body of the present disclosure is a plasma surface-treated product or a base surface-treated product obtained by applying voltage to the biodegradable polymer microparticles for a filler to induce a discharge to the plasma surface-treated biodegradable polymer micropar- ticle and discharging the biodegradable polymer micropar- ticle.

Figure 4:
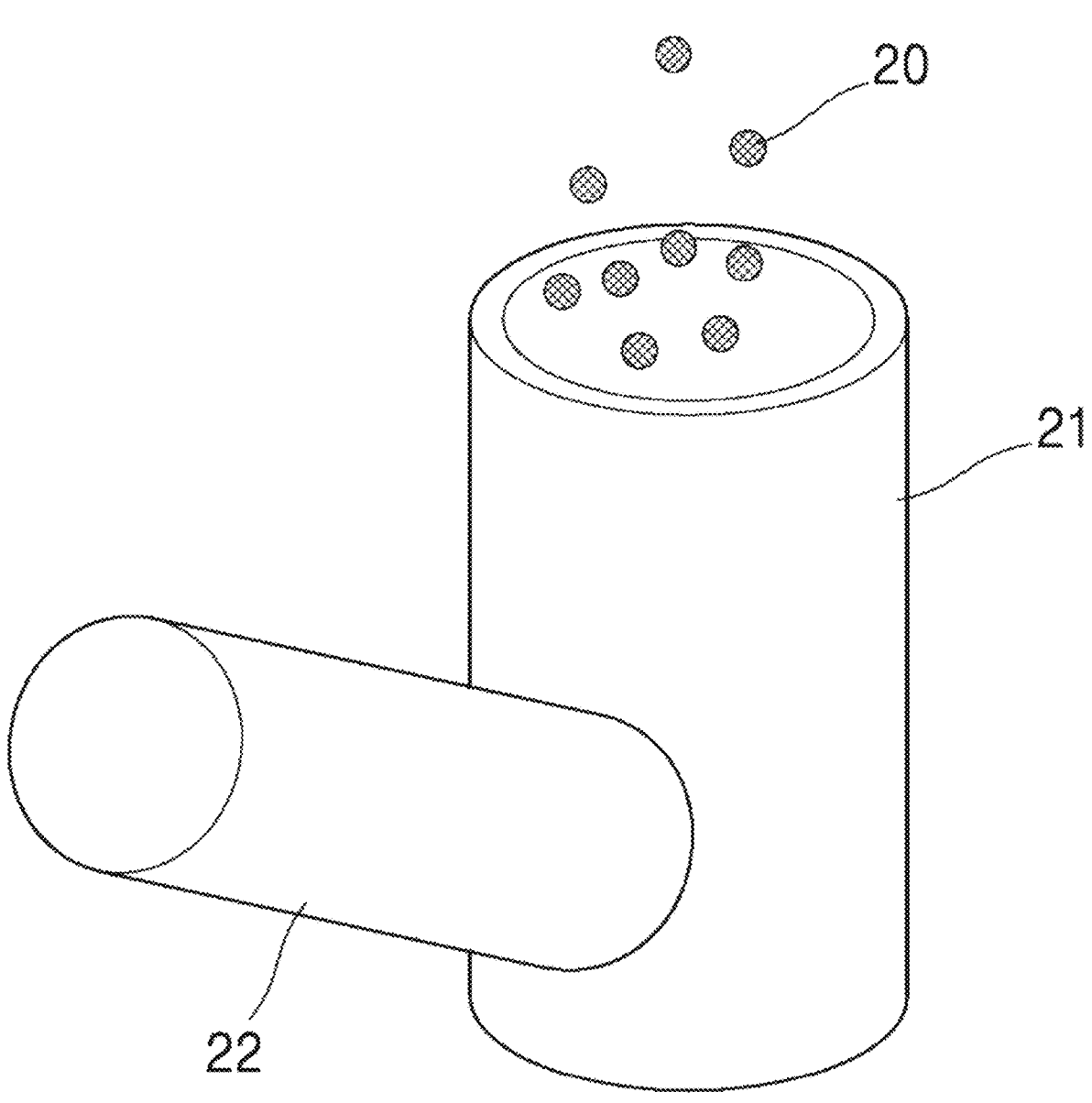
FIG. 4 is a schematic diagram of the plasma reaction device of FIG. 3.
Figure 5:
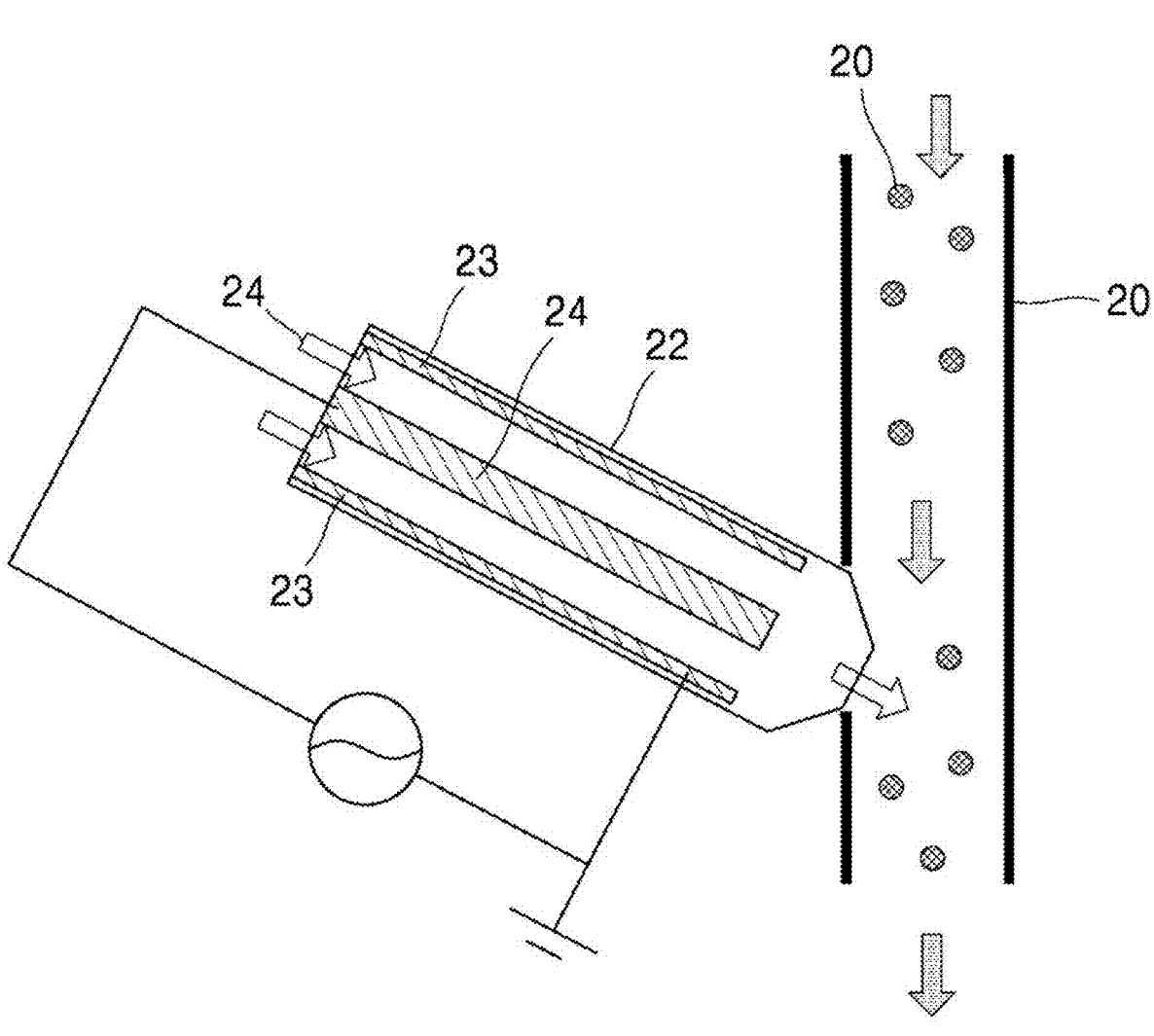
FIG. 5 is a side view of the plasma reaction device of FIG. 3.

The discharge for plasma surface-treatment can be per- formed using a plasma reaction device of FIGS. 3 to 5. The discharge processing time is, for example, one second to one minute.

When the biodegradable polymer microparticle is sur- face-treated using a general plasma reaction apparatus, it is difficult to fix microparticles to a plasma device if the average particle diameter of the biodegradable polymer microparticle is 20 to 50 μm, 22 to 48 μm, 25 to 45 μm, or 30 to 40 μm. So, it is substantially difficult to perform effective surface treatment.

However, when the biodegradable polymer microparticle having an average particle diameter of 20 to 50 μm is plasma-treated using the plasma reaction device of FIGS. 3 to 5 of the present disclosure, the hydrophilic surface treatment can be effectively performed to the biodegradable polymer microparticle without any problem.

When treating the surface with plasma, if the voltage is in the range, a hydrophilic group is effectively induced to the biodegradable polymer microparticle so as to effectively prevent self-aggregation of the biodegradable polymer microparticle by lapse of time.

The surface treatment using the plasma device of the present disclosure includes the operations of: supplying air to the inside of a reactor, for example, through a gas supply unit; applying voltage to an electrode to which a power supply unit is connected to cause electric discharge to the inside of a plasma discharge unit; making plasma-treated air come into direct contact with the biodegradable polymer microparticle in the plasma discharge unit so as to surface- treat the biodegradable polymer microparticle. Here, other gas may be used instead of air.

In a plasma generator, air is injected at 400 to 600 mL/min or 450 to 550 mL/min, and alternating current of 300 Hz to 500 Hz, 320 Hz to 480 Hz, or 350 Hz to 450 Hz is applied to the electrode to which the power supply unit is connected, so that plasma-treated air comes into contact with the biodegradable polymer microparticle.

In addition, the freeze-dried body of the present disclosure is a base surface-treated product of the biodegradable poly- mer microparticles for a filler.

The base uses, for example, a sodium hydroxide solution. The concentration of sodium hydroxide is not specifically limited, but is 0.1 to 5% by weight, 0.2 to 3% by weight, or 0.5 to 2% by weight.

The base surface-treated biodegradable polymer microparticle is manufactured through the operations of: adding 0.1 to 5% by weight of a sodium hydroxide solution having concentration of 0.1 to 5% by weight, 0.2 to 3% by weight, or 0.2 to 1% by weight to the biodegradable polymer microparticle for a filler, and stirring the same for 10 to 60 seconds; and washing and vacuum-drying the resultant. Here, the content of sodium hydroxide is 0.1 to 5 parts by weight, or 0.1 to 3 parts by weight, based on 100 parts by weight of the biodegradable polymer microparticle for filler. If the content of sodium hydroxide and the surface treatment time are in the above-mentioned range, the content of the biocompatible carrier, which is an excipient, is in a range of 1 to 5 parts by weight, based on 100 parts by weight of the total weight of the freeze-dried body, thereby effectively preventing self-aggregation of the biodegradable polymer microparticles and having excellent dispersion stability. The total weight of the freeze-dried body means 100 parts by weight of the total weight of the biodegradable polymer microparticles and the biocompatible carrier.

For example, if polydioxanone (PDO), which is a biode- gradable polymer microparticle for a filler, is surface-treated with a sodium hydroxide solution, a part of the PDO is decomposed to $CH_3CH_2OCH_2C(=O)OH$ and ethanol. When the product is washed and vacuum-dried, at least one selected from the groups consisting of polydioxanone (PDO), poly-lactic acid (PLA), poly-L-lactic acid (PLLA), poly-D-lactic acid (PLA), poly-ε-caprolactone (PCL), polyglycolic acid (PGA), copolymers thereof, and mixtures thereof having a carboxyl group on the surface thereof is induced onto the surface of the PDO. The structure can be confirmed through an infrared spectroscopic spectrum.

The PDO having the carboxyl group on the surface thereof, for example, the PDO having $CH_3CH_2OCH_2C(=O)OH$ or $CH_3CH_2OCH_2C(=O)O-$ induced on the sur- face thereof, has not only excellent dispersibility for one or more solvents selected from injection water, sterilized water, and distilled water while using a small amount of excipient, and effectively prevents self-aggregation of the PDO having the carboxyl group on the surface, thereby improving dis- persion stability.

The particle diameter ($D_{10}$) of the surface-treated biode- gradable polymer microparticle in the freeze-dried body for a filler and the filler injection of the present disclosure is 10 to 20 μm, and the particle diameter ($D_{90}$) of the surface- treated biodegradable polymer microparticle is 60 to 70 μm. Here, the average particle diameters ($D_{50}$), ($D_{10}$), and ($D_{90}$) are measured by using a laser diffraction scattering type particle size analyzer (PSA).

In the filler injection According to an embodiment of the present disclosure, the content of the hydrophilic biodegrad- able polymer microparticles is 8 to 9 parts by weight, for example, 8.1 to 8.8 parts by weight, the content of the biocompatible carrier is 1 to 2 parts by weight, for example, 1.2 to 1.8 parts by weight, and the content of at least one selected from the injection water, the sterilized water, and distilled water is 85 to 95 parts by weight, 88 to 92 parts by weight, for example, 90 parts by weight.

In view of obtaining filler injection having excellent dispersibility, it is desirable to satisfy the following formula in connection with a 10% cumulative diameter ($D_{10}$), 50% cumulative diameter ($D_{50}$), and 90% cumulative diameter ($D_{90}$) obtained from a particle size distribution measurement value.

$$0.8 \leq (D_{90} - D_{10})/D_{50} \leq 3.5 \qquad \text{[Formula 1]}$$

$(D_{90} - D_{10})/D_{50}$ is 1.0 to 3.4, 1.5 to 3.2, or 2.0 to 3.0.

In the present specification, $D_{90}$, $D_{50}$, and $D_{10}$ can be obtained by measuring a particle size distribution by using the laser diffraction scattering type particle size analyzer. A median diameter ($D_{50}$) of a cumulative volume measured from a particle size distribution diagram is calculated, and the calculated diameter becomes an average diameter. In addition, the biodegradable polymer microparticle of the present disclosure has very excellent uniformity in size.

Additionally, a powder-water contact angle value for the surface-treated biodegradable polymer microparticle is 50° or less, 5 to 36° for example, 36.2 to 36.7°. If the powder-water contact angle is in the aforementioned range, it means that the surface of the biodegradable polymer microparticle is hydrophilic, and as such, it is possible to manufacture a filler injection having excellent dispersibility without using an excipient.

The powder-water contact angle value for the biodegradable polymer microparticle is evaluated according to the following method.

The powder-water contact angle is measured by using a dynamic contact angle measuring device. For the measurement, microparticles fill a glass tube with the inner diameter of 1.2 cm up, and then, the glass tube is erected on the floor filled with sufficient water.

After that, after waiting until the water drawn by the capillary force is raised no longer, the water level in the tube and a radius of a meniscus are measured so as to trace a water contact angle based on the measured value (Siebold et al., Effect of dynamic contact angle on capillary rise phenomena, Colloids and surfaces, 2000).

The biodegradable polymer of the present disclosure is at least one selected from the groups consisting of polydioxanone (PDO), poly-lactic acid (PLA), poly-L-lactic acid (PLLA), poly-D-lactic acid (PLA), poly-ε-caprolactone (PCL), polyglycolic acid (PGA), copolymers thereof, and mixtures thereof, and especially, uses polydioxanone. Moreover, the number average molecular weight (Mn) of the biodegradable polymer is 50,000 to 500,000 Daltons, or 50,000 to 200,000 Daltons. If the number average molecular weight of the biodegradable polymer is less than 50,000 Daltons, since the decomposition speed of the biodegradable polymer microparticles is increased, it is not suitable as a biomaterial for a filler. If the number average molecular weight of the biodegradable polymer exceeds 500,000 Daltons, it is difficult to manufacture particles having uniform size and quality since processing is difficult due to high viscoelasticity.

The filler injection manufactured according to one embodiment is characterized by dispersing 1 g of hydrophilic surface-treated biodegradable polymer microparticles for a filler into 10 ml of one or more selected from injection water, sterilized water, and distilled water, and proceeding precipitation of the biodegradable polymer microparticle for a filler. Accordingly, the surface-treated biodegradable polymer microparticle of the present disclosure has very excellent dispersibility in the filler injection.

According to an embodiment of the present disclosure, when sodium carboxy cellulose is used as the biocompatible carrier used in manufacturing the freeze-dried body for a filler of the present disclosure and the biodegradable polymer microparticle is polydioxanone, it is preferable to control the water content to be 0.5 to 1.5% by weight by drying the freeze-dried body. When sodium carboxy cellulose is used as the biocompatible carrier, the solubility of the freeze-dried body in water is high. However, when products are manufactured by using the freeze-drying body, if the water content in the products exceeds a predetermined level, cellulose returns to the hydroxyl functional group within a few months to one year, thereby lowering the solubility of the freeze-dried body to water.

Therefore, in the case of the freeze-dried body which uses polydioxanone as the biodegradable polymer microparticle and uses sodium carboxymethyl cellulose as the biocompatible carrier, it is preferable to control the moisture content of the freeze-dried body to be 1% by weight or less, for example, 0.5 to 1% by weight. When the moisture content of the freeze-dried body is in the above-mentioned range, safety of the freeze-dried body can be improved, for example, for at most 2 years.

The operation of controlling the moisture content of the freeze-dried body in the above-mentioned range is carried out, for instance, according to a process of controlling the moisture content of the freeze-dried body to the above-mentioned range by storing, for example, in a desiccator with a moisture absorbent. Here, the moisture absorbent is highly hygroscopic like silica gel or the like.

Hereinafter, a method for manufacturing a biodegradable polymer microparticle for a filler, which is a starting material used for manufacturing a freeze-dried body for a filler and filler injection will be described.

The method for manufacturing a biodegradable polymer microparticle for a filler includes the operations of: providing a first composition containing organic solvent miscible with water, and biodegradable polymer microparticles; providing a second composition containing surfactant and water; preparing mixture by mixing the first composition and the second composition; stirring the mixture to prepare a third composition containing polymer microparticles; separating the polymer microparticles from the third composition; and sorting polymer microparticles, of which the average particle diameter is 20 to 50 μm, from the separated polymer microparticles. When the first composition containing organic solvent miscible with water and the second composition containing surfactant are mixed, a biodegradable polymer microparticle having a particle diameter of 20 μm to 100 μm suitable for a face filler and improved particle diameter uniformity can be manufactured simply at a high yield.

First, the first composition containing organic solvent miscible with water is prepared. The first composition can be prepared by dissolving a biodegradable polymer, for example, in an organic solvent.

The biodegradable polymer contained in the first composition may be one or more selected from the groups consisting of polydioxanone (PDO), poly-lactic acid (PLA), poly-L-lactic acid (PLLA), poly-D-lactic acid (PLA), poly-ε-caprolactone (PCL), polyglycolic acid (PGA), copolymers thereof, and mixtures thereof, and especially, uses polydioxanone. The copolymer may be, for example, a polylactic acid-glycolic acid copolymer, a polydioxanone-caprolactone copolymer, a folate-caprolactone copolymer, and the like. The biodegradable polymer is, for example, polydioxanone.

The number average molecular weight (Mn) of the biodegradable polymer contained in the first composition is, for example, 50,000 to 500,000 Daltons, 50,000 to 300,000 Daltons, or 50,000 to 200,000 Daltons. When the number average molecular weight of the biodegradable polymer is less than 50,000 Daltons, since the decomposition speed of the biodegradable polymer microparticles can be increased, the biodegradable polymer microparticle is not suitable as a biomaterial for a filler. If the number average molecular weight of the biodegradable polymer exceeds 500,000 Daltons, it is difficult to manufacture particles having a uniform size and quality since processing is difficult due to high viscoelasticity.

The content of the biodegradable polymer comprising the first composition is, for example, 0.1 to 20% by weight, 0.1 to 10% by weight, 1 to 10% by weight, 3 to 9% by weight, or 4 to 8% by weight with respect to the entire first composition. If the content of the biodegradable polymer including the first composition is too low, the content of the biodegradable polymer including the first composition gets extremely low to deteriorate manufacturing efficiency of the polymer microparticles. If the content of the biodegradable polymer containing the first composition is too high, it is difficult to obtain polymer microparticles having a uniform size.

The first composition may be free of surfactant. The first composition can easily form uniform polymer microparticles without including, for example, surfactant. The first composition may not include, for example, an additive having interfacial activity at the interface between the first composition and the second composition. Since the first composition does not include the surfactant, manufacturing of the polymer microparticles is simplified, and the polymer microparticles having low impurity content can be manufactured. Therefore, the biocompatibility of the polymer microparticles manufactured by using the first composition is further improved.

The organic solvent containing the first composition is organic solvent miscible with water. In this specification, the "organic solvent miscible with water" is organic solvent that is completely or partially mixed with water. The organic solvent miscible with water means organic solvent that does not form a separate phase differentiated from, for example, water. In this specification, the organic solvent, which is miscible with water, is solvent having 3 g or more, 5 g or more, 10 g or more, or 50 g or more of solubility to 100 g of water at 20° C. Therefore, the manufacturing method of the present disclosure is differentiated from a conventional manufacturing method using organic solvent which is not miscible with water.

The organic solvent contained in the first composition may be one or more selected from halogenated alcohol, halogenated hydrocarbon, aromatic hydrocarbon, aliphatic hydrocarbon, aliphatic alcohol, aliphatic amide, aliphatic ketone, aliphatic ether, and aliphatic aldehyde. The organic solvent contained in the first composition may be one or more selected from the groups consisting of HFIP (1,1,1,3, 3,3-Hexafluoro-2-propanol), acetone, acetonitrile, acetic acid, dioxane, ethanol, methanol, isopropyl alcohol (IPA), propanol, tetrahydrofuran (THF), pentane, and mixtures thereof. For example, if polydioxanone is used as a biodegradable polymer contained in the first composition, fluorinated alcohol can be used as the organic solvent for dissolving polydioxanone. The fluorinated alcohol is, for example, 1,1,1,3,3,3-hexafluoro-2-propanol.

The boiling point of the organic solvent contained in the first composition may be, for example, from 10 to 100° C., 20 to 90° C., or 30 to 80° C. The organic solvent can be easily volatilized since having the boiling point in the above-mentioned range. If the boiling point of the organic solvent is too low, it is difficult to maintain the liquid phase, and if the boiling point of the organic solvent is too high, evaporation of the organic solvent becomes difficult and the content of the residual solvent is increased, thereby deteriorating biocompatibility of the biodegradable polymer microparticle.

The content of the organic solvent contained in the first composition is, for example, 50 to 99.999% by weight, 60 to 99.9 wt %, 70 to 99.9 wt %, 80 to 99.9 wt %, or 90 to 99.9 wt %, based on the total weight of the first composition. If the content of the organic solvent contained in the first composition is too low, uniform polymer microparticles may not be obtained due to the increased viscosity of the first composition. If the content of the organic solvent contained in the first composition is too high, the content of the polymer microparticles generated from the first composition is so low that the production efficiency of the polymer microparticles may be deteriorated.

Moreover, a second composition containing surfactant and water is provided. The second composition can be prepared by dissolving one or more surfactants selected from water-soluble polymers and water-soluble monomers in at least one selected from water and alcohol.

In this specification, the aqueous solution is a composition containing water, and is not necessarily limited to 100%. The content of water in the solvent is at least 50% by weight, at least 60% by weight, at least 70% by weight, at least 80% by weight, or at least 90% by weight. The solvent contained in the second composition is, for example, water.

The surfactant contained in the second composition may be at least one selected from a water-soluble polymers, such as Polyvinyl alcohol, polyoxyethylene sorbitan and its salt, and water-soluble monomers, such as soybean lecithin, monoglyceride, etc.

The content of the surfactant contained in the second composition may be, for example, 1 to 10% by weight, 3 to 9% by weight, or 4 to 8% by weight with respect to the entire second composition. If the content of the surfactant is too low, the interface activity of the surfactant is weakened so that it is difficult to manufacture polymer microparticles having a uniform size. If the content of the surfactant is too high, the size of the polymer microparticles is excessively reduced so that it cannot act as a filler by being searched by macrophages in the living body or the size of the polymer microparticle is increased due to aggregation of the polymer microparticles. When polyvinyl alcohol, which is a water-soluble polymer, is used as surfactant contained in the second composition, water or a water-and-alkyl alcohol mixed solution can be used as the solvent in which polyvinyl alcohol is dissolved.

When a water-soluble polymer is used as surfactant contained in the second composition, the number average molecular weight of the water-soluble polymer may be, for example, 50,000 to 200,000 Daltons, 70,000 to 170,000 Daltons, or 100,000 to 150,000 Daltons. If the number average molecular weight of the water-soluble polymer is less than 50,000 Daltons, the interface activity may be deteriorated. If the number average molecular weight of the water-soluble polymer exceeds 200,000 Daltons, it is difficult to form uniform polymer microparticles due to a high concentration.

The second composition may further include other surfactants besides the surfactant described above. The other surfactants additionally included in the second composition may be anionic surfactant, cationic surfactant, or amphoteric surfactant. The other surfactants additionally included in the second composition may be one selected from, for example, polyoxyethylene sorbitan monolaurate (Tween 20), polyoxyethylene sorbitan monopalmitate (Tween 40), polyoxyethylene sorbitan monostearate (Tween 60), polyoxyethylene sorbitan monooleate (Tween 80), and polyoxyethylene sorbitan trioleate (Tween 85), but are not limited thereto, and anything is possible if used as surfactant in the relevant technical field. The second composition is provided to manufacture polymer microparticles having uniform particle size suitable for a filler at a high yield even if other surfactants are not additionally included.

The pH of the second composition may be at least 5.0, at least 5.5, at least 6.0, or at least 6.5. The pH of the second composition may be, for example, 5.0 to 8.0, 5.0 to 7.5, 5.0 to 7, or 5 to 6.5. Since the second composition has pH in the above-mentioned range, polymer microparticles having a uniform size can be manufactured at a high yield.

Next, the first composition and the second composition are mixed together so as to prepare a mixture.

In the operation in which the mixture is prepared, the organic solvent and water can be mixed in a ratio of 50 to 200 parts by volume of water contained in the second composition with respect to 100 parts by volume of the organic solvent contained in the first composition. For example, the mixing volume ratio of the organic solvent and water is 1:0.5 to 1:2, 1:0.6 to 1:1.9, 1:0.6 to 1:1.8, 1:0.7 to 1:1.7, 1:0.7 to 1:1.6, 1:0.7 to 1:1.5, 1:0.8 to 1:1.4, 1:0.8 to 1:1.3, or 1:0.8 to 1:1.2. In the operation of preparing the mixture, 100 parts by volume of the organic solvent and 50 to 200 parts by volume of water are mixed. So, the used amount of water is significantly reduced compared to a conventional manufacturing method in which 100 parts by volume of the organic solvent and 800 parts by volume of water are mixed. Furthermore, in the conventional manufacturing method in which 100 parts by volume of an organic solvent and 800 parts by volume of water are mixed, it is difficult to manufacture polymer microparticles having a uniform particle diameter since the first composition is added to an excess of water and rapid precipitation of biodegradable polymers is performed. On the other hand, in the manufacturing method of the present disclosure in which organic solvent and water are mixed in a similar volume ratio, polymer microparticles having a uniform particle diameter can be easily manufactured by slowly proceeding with the precipitation of biodegradable polymers. In addition, compared with the conventional art using an excess amount of solvent, the present disclosure can remarkably reduce a used amount of solvent and manufacture polymer microparticles more simply.

The content of the surfactant in the mixture is 10 to 50 parts by weight, 15 to 45 parts by weight, or 20 to 35 parts by weight based on 100 parts by weight of the biodegradable polymer microparticles.

Next, the mixture is stirred so that a third composition containing polymer microparticles is prepared. Mixing the first composition and the second composition and stirring the mixture can be performed sequentially or substantially simultaneously. For example, a mixture is prepared by simultaneously or sequentially injecting the first composition and the second composition into a container in which an agitator rotates, and stirring can be performed at the same time.

Stirring of the mixture may be performed at 100 to 800 rpm, 100 to 700 rpm, 200 to 700 rpm, 200 to 600 rpm, 300 to 600 rpm, or 300 to 500 rpm. If stirring (e.g., stirring speed, RPM) of the mixture is too slow, mixing of the first composition and the second composition may not be smoothly performed. If stirring (e.g., stirring speed, RPM) of the mixture is too fast, the uniformity of the particle size of the polymer microparticles may be reduced.

Stirring of the mixture may be performed for at least one day, namely, 24 hours. Since stirring of the mixture is performed for a long time, the organic solvent is volatilized slowly, so that the biodegradable polymer can be gradually precipitated into polymer microparticles in a uniform condition. Therefore, the uniformity of the particle size of the polymer microparticles can be improved. Since the stirring of the mixture is at a low speed of 800 rpm or more, the precipitation of the polymer microparticles may not be sufficiently performed if the stirring time is less than one day, namely, 24 hours. The stirring time of the mixture may be, for example, 1 to 10 days, 2 to 9 days, 3 to 8 days, 3 to 7 days, or 4 to 6 days. When the stirring time of the mixture is excessively increased, the manufacturing efficiency of the polymer microparticles may be deteriorated.

Next, the polymer microparticles are separated from the third composition. The method for separating polymer microparticles from the third composition is not particularly limited thereto, may include filtration, precipitation, washing, and the like, but is not limited thereto.

The operation of separating the polymer microparticles from the third composition may include operations of: precipitating and separating polymer microparticles from the third composition; and washing the separated polymer microparticles several times.

After stirring is finished, the third composition is left for at least 1 hour, at least 2 hours, at least 5 hours, at least 12 hours, or at least 24 hours to remove supernatant and separate the polymer microparticles. Next, the separated polymer microparticles are mixed with distilled water and stirred at 100 to 1000 rpm for 1 to 24 hours, and then a washing process for removing steam can be performed at least once. Through the washing process, impurities remaining in the polymer microparticles can be effectively removed.

The manufacturing method of the present disclosure may not include the operation of stabilizing in a stabilizer or stabilizing solution. Therefore, the manufacturing of polymer microparticles is more simplified. Conventional manufacturing methods consume lots of time and solvent since including the operation of stabilizing in an excess of alcohol or in an excess of surfactant solution for a long time in order to stabilize or mature the manufactured polymer microparticles. On the other hand, the present disclosure can remarkably reduce manufacturing time and a used amount of solvent since obtaining polymer microparticles by separating and/or washing after preparing the third composition containing polymer microparticles without the stabilization operation.

The average particle diameter ($D_{50}$) of the polymer microparticles manufactured by the manufacturing method of the present disclosure can be 20 um to 50 um, 21 um to 49 um, 23 um to 50 um, 23 um to 45 um, or 25 to 45 um. The polymer microparticles may have a size suitable for application to a filler by having an average particle diameter in the above-mentioned range. If the average particle diameter of the polymer microparticle is too small, the polymer microparticle cannot act as a filler by being searched by macrophages. If the average particle diameter of the biodegradable polymer microparticle exceeds 300 μm, it may not be suitable for injection. For example, if the average particle diameter of the polymer microparticles is excessively increased, because the diameter of the injection needle required for filler injection is increased, it may increase side effects, such as scars, pains caused by a procedure. Additionally, in the case of a face filler, it is very important to accurately control the volume of the face by being injected into the face, but the accurate volume control may be difficult due to an increase of the particle size of the filler. The size of the biodegradable polymer microparticles used in the face filler can be 40 to 100 um. The size of the biodegradable polymer microparticles used not for the face but for other purposes can be, for example, 100 to 300 um.

The content of the polymer microparticle having the particle size of 25 um to 75 um, among polymer microparticles manufactured by the manufacturing method, may be 50% by volume or more, 55% by volume or more, 60% by volume or more, 65% by volume or more, 70% by volume or more, 75% by volume or more, or 80% by volume or more. Therefore, the polymer microparticles having a size suitable for the face filler by the manufacturing method can be simply manufactured without any additional process, such as filtration, classification, etc., at a high yield.

In the operation of sorting polymer microparticles having an average particle diameter of 20 to 50 mm from the polymer microparticles separated when the biodegradable polymer microparticles are manufactured, the biodegradable polymer microparticles can be classified by sizes in a dry type or a wet type, for example, using a size sieving machine. In the case of a wet-type sorting, freeze-drying is additionally performed to remove moisture and then classify the polymer microparticles. However, the method for manufacturing polymer microparticles of the present disclosure can manufacture particles having a size in the range of 25 to 50 um at a high yield without such a classification process.

The biodegradable polymer microparticle for filler is provided to be used for wrinkle improvement, facial molding, body molding, male prosthesis, or urinary incontinence treatment.

In another aspect of the present disclosure, provided are a freeze-dried body for a filler and a method for manufacturing filler injection using the same.

The filler injection is manufactured through the operations of: preparing a biodegradable polymer microparticle for a filler having an average particle diameter of 20-50 μm; surface-treating the biodegradable polymer microparticle with plasma or base to manufacture a surface-treated biodegradable polymer microparticle; dissolving the hydrophilic surface-treated biodegradable polymer microparticle, the biocompatible carrier, and distilled water to obtain a mixed solution; and freeze-drying the mixed solution to obtain a freeze-dried body.

The freeze-drying can be carried out at temperature of −70° C. to −20° C. The freeze-drying time is, for example, 1 to 72 hours, 5 to 48 hours, or 15 to 24 hours. The cooling rate of the freeze-drying is −3° C./min to −2° C./min.

Before the freeze-drying, pre-freeze-drying may be further performed. The pre-freeze-drying can be carried out at −75° C. to −65° C. The pre-freeze-drying time may be varied according to pre-freeze-drying temperature, and for example, the pre-freeze-drying can be performed for 1 to 72 hours, 5 to 48 hours, or 15 to 24 hours.

The freeze-dried body obtained through the above process can be manufactured as filler injection through an operation of hydrating the freeze-dried body obtained according to the above process in at least one selected from injection water, sterilized water, and distilled water. For the filler injection, 1 g of freeze-dried body is dispersed in 10 ml of one or more selected from injection water, sterilized water, and distilled water, and then, the biodegradable polymer microparticle for a filler is precipitated after 60 minutes. The content of the freeze-dried body in the filler injection is 1 to 10 parts by weight based on the total weight of the filler for filler. The viscosity of the filler injection is 50 to 2000 cP, 100 to 1500 cP, or 150 to 1200 cP. When the viscosity of the filler is in the above-mentioned range, the degree of satisfaction of the treatment is increased due to excellent dispersibility and proper injection pressure.

The content of the surface-treated biodegradable polymer microparticles in the filler injection can be 10 to 80% by weight, 10 to 50% by weight, 10 to 30% by weight, or 15 to 30% by weight with respect to the entire filler injection. If the content of the biodegradable polymer microparticles is less than 10% by weight, it is difficult to disperse evenly due to low concentration. If the content of the biodegradable polymer microparticles exceeds 80% by weight, it is difficult to perform freeze-drying and mixing with the biocompatible carrier due to low moisture content.

The present disclosure can manufacture filler injection without using an excipient.

The surface-treated biodegradable polymer microparticles can be used as injection by hydrating at least one selected from injection water, sterilized water, and distilled water.

The biodegradable polymer filler can be, for example, a spherical porous particle, but is not limited thereto and can be selected according to required conditions. The biodegradable polymer filler can be easily hydrated in water by the capillary phenomenon due to the spherical porous shape.

The spherical porous particle may have density of, for example, 0.2 to 0.9 g/cm$^2$, 0.2 to 0.8 g/cm$^2$, 0.2 to 0.7 g/cm$^2$, 0.2 to 0.6 g/cm$^2$, or 0.2 to 0.5 g/cm$^2$. The spherical porous particle can be easily and quickly hydrated in water by having density of the above-mentioned range. The spherical porous particle may have an average diameter of 3 to 8 mm, 3 to 7 mm, and 3 to 6 mm. The spherical porous particle can facilitate storage and improve workability since having the particle diameter in the above-mentioned range.

The manufacturing method can further include an operation of preparing spherical porous particles by removing moisture and sterilizing the spherical porous particles.

The sterilization is gamma-ray sterilization, ethylene oxide sterilization, or decompression sterilization, but is not limited thereto, and any sterilization method used in the relevant technical fields is applicable.

Since the biodegradable polymer microparticle is in the form of a spherical porous particle, hydration is rapidly progressed and injection is manufactured easily. The injection manufactured by the above-mentioned method has viscosity of 8,000 to 30,000 cPs at 25 É, and an extrusion power is 5N to 12N.

Alternatively, the biodegradable polymer microparticle may be in the form of dry powder.

FIGS. 3 to 5 are schematic views of a plasma device using a plasma generator used for hydrophilic surface treatment of the biodegradable polymer microparticles of the present disclosure.

FIG. 3 is a block diagram of the present disclosure. Referring to FIG. 3, air, helium, argon, nitrogen gas, or mixed gas thereof for maintaining discharge is supplied to a plasma reaction device 14 in a gas control unit 12, and electricity is applied from a power supply unit 10 supplying a medium frequency (MF) power source having frequencies of tens of to hundreds of kHz so that plasma is generated from a plasma reaction device 14. The generated plasma carries out surface treatment of a composition in which biodegradable polymer microparticles are contained, ozone is generated by discharge, and after the use, gases are discharged out by an exhaust system 16 around the electrode. The composition in which biodegradable polymer microparticles are contained is manufactured by being mixed with hexafluoro-2-isopanol, which is solvent. Here, the content of the solvent is 3 to 6 parts by weight based on 100 parts by weight of the biodegradable polymer microparticles.

The electrode is made of metal, such as an aluminum alloy, stainless steel, or the like, and in particular, a power electrode may be made of tungsten. The thickness and width of the electrode is 70 mm to 300 mm so as to generate an optimal plasma according to the use purposes.

The supplied gases are nitrogen, nitrogen and trace oxygen, compressed air, etc. Nitrogen is generally selected as carrier gas, and less than 3% of oxygen is supplied as reaction gas.

FIG. 4 is a schematic view of a discharge device of FIG. 4, and FIG. 5 is a side view of the discharge device of FIG. 4.

In FIG. 5, the plasma reaction device 22 of the present disclosure applies power to the electrodes 23 from the power supply unit and generates plasma between the electrodes 24 and the gas 24 supplied from the gas control unit 12. The biodegradable polymer microparticles 20 are supplied to the reactor 21, and the plasma of the plasma reaction device 22 comes into direct contact with the surface of the biodegradable polymer microparticles 20.

Ozone which can be generated in the already-used gas and the high-frequency discharge can be discharged to the outside by exhaust systems 16 installed at the left and right sides of the bottom electrode.

A heating system is installed in the gas supply unit 12 to increase temperature of gas according to circumstances, and a low voltage is applied from the MF power supply 10 to the electrode so as to generate plasma.

Using the surface treatment method of the present disclosure, hydrophilic surface-treated biodegradable polymer microparticles can be manufactured.

The hydrophilic surface treatment of the biodegradable polymer microparticles can be effectively performed by using the plasma device of FIGS. 3 to 5. The plasma device can prevent surface residual of chemical ingredients, which can be generated during surface treatment using an aqueous sodium hydroxide aqueous solution and reform the entire surface uniformly. Moreover, if the size of the biodegradable polymer microparticle is less than 20 μm, a general plasma device cannot easily perform the surface treatment. There is the reason that it is difficult to perform desired surface treatment since it is difficult to fix microparticles by the injection pressure when plasma gas is injected using the general plasma device. However, the plasma device according to the present disclosure can prevent the above-mentioned problem and allow a user to easily perform surface treatment of biodegradable polymer microparticles.

Hereinafter, examples of the present disclosure will be described in more detail. The following examples are just illustrated for assisting understanding of the present disclosure, and the scope of the present disclosure is not limited thereto.

(Manufacturing Biodegradable Polymer Microparticles)

Preparation Example 1: Preparation of Polydioxanone Microparticles 5 g of polydioxanone (PDO) with intrinsic Viscosity (IV) of 1.55 dL/dg and number average molecular weight of 100,000 Daltons as biodegradable polymer was dissolved in 100 ml of Hexafluoroisopropanol (HFIP), which is an organic solvent, to prepare a first composition.

1.5 g of polyvinyl alcohol (PVA) with number average molecular weight of 130,000 Daltons was dissolved in 150 ml of distilled water so that second composition with about pH 5.5 was prepared as surfactant.

The first composition and the second composition were mixed at a volume ratio of 1:1 to prepare a third mixture. The prepared mixture was stirred at 400 rpm for 5 days to evaporate the organic solvent, thereby obtaining a third composition containing polymer microparticles.

After stirring, the polymer microparticles were left as they were for 24 hours so that the polymer microparticles were settled, and then, the supernatant was removed, and the polymer microparticles were separated.

Purified water was added to the separated polymer microparticles and then was stirred again to be washed. The washing operation was performed three times to manufacture polymer microparticles.

The polymer microparticles obtained through the above process were placed on a sieve having holes of 20 μm size for at least six hours to primarily remove water. Then, completely dried microparticles having an average particle diameter of 20 to 200 μm were obtained through a drying process in a vacuum dryer (5 Pa or less) for at least two days.

The dried microparticles were obtained when the PDO microparticles having the size range as illustrated in the following Table 1 were sorted through various sizes of sieve.

The average particle diameter ($D_{50}$) of the PDO microparticles of the preparation example 1 is 20 to 50 μm.

Preparation Example 2

Except that, instead of polydioxanone, Poly-L-L-Lactic acid (PLLA) with inherent viscosity (IV) of 0.8 to 1.2 dL/dg and number average molecular weight of 80,000 to 120,000 Daltons were used as the biodegradable polymers, PLLA microparticles having the average particle diameter of 20 to 50 μm were manufactured in the same manner as the preparation example 1.

Preparation Example 3

Except that, instead of polydioxanone, Poly-ε-caprolactone (PCL) with inherent viscosity (IV) of 0.8 to 1.0 dL/dg and number average molecular weight of 80,000 to 110,000 Daltons were used as the biodegradable polymers, PCL microparticles having the average particle diameter of 20 to 50 μm were manufactured in the same manner as the preparation example 1.

Comparative Preparation Example 1

According to the preparation example 1, completely dried microparticles having the average particle diameter of 20 to 200 μm were obtained.

As the dried microparticles, PDO microparticles having the average particle diameter of 20 to 100 μm presented in the following Table 1 through various sizes of sieves.

Comparative Preparation Example 2

According to the preparation example 1, completely dried microparticles having the average particle diameter of 20 to 200 μm were obtained.

As the dried microparticles, PDO microparticles having the average particle diameter ($D_{50}$) of 100.01 to 200 μm presented in the following Table 1 through various sizes of sieves.

TABLE 1

| | Preparation example 1 | Comparative preparation example 1 | Comparative preparation example 2 |
|---|---|---|---|
| Average particle diameter of PDO microparticle $(D_{50})$ ($\mu$m) | 20~50 | 20~100 | 100.01~200 |

(Manufacturing of Surface-Treated Biodegradable Polymer Microparticle, Freeze-Dried Body, and Filler Injection Using the Same)

Example 1

The PDO microparticles manufactured according to the preparation example 1 were placed in 0.5% by weight of a NaOH aqueous solution, stirred at 200 rpm, and surface-treated in a wet type for one minute. Here, the content of NaOH was 5 parts by weight based on 100 parts by weight of PDO microparticles.

After that, the mixed solution was poured into a sieve having a 20 $\mu$m-sized hole to separate the surface-treated microparticles. A total of 30 ml of purified water was further poured into the reactor to remove the residual NaOH aqueous solution. The carboxyl group dried through 24-hour vacuum drying (internal pressure of drier: 8 to 10 Pa, especially, about 9 Pa) was induced onto the surface, so that hydrophilic surface treated PDO microparticles were obtained. Here, the carboxyl group is, for example, $CH_3CH_2OCH_2C(=O)OH$. When the ester is basic hydrolyzed, the carboxylic acid and the alcohol were decomposed into carboxylic acid and alcohol, and when the PDO-based microparticles having the same functional group were used, self-aggregation was prevented.

When hydrophilic surface-treated polydioxanone microparticles and 1 g of carboxymethyl cellulose CMC (standard viscosity: 2% solution reference, 1125-2100 cc), which was an excipient (biocompatible carrier), were added and dissolved in 100 ml of water so as to manufacture a mixed solution. The mixed weight ration of the hydrophilic surface-treated polydioxanone microparticles and the CMC in the mixed solution is 95:5.

The mixed solution of a predetermined amount was poured into a hemispherical mold having a height of 5 mm, was put into a freezer which had internal temperature of $-75°$ C. to suddenly cool and freeze the mixed solution, and then, was freeze-dried for 24 hours using a freeze-drier to manufacture a freeze-dried body for a filler.

The pre-freeze-dried body was put in the freezer which had internal temperature of $-20°$ C. to freeze-dry the pre-freeze-dried body for 24 hours using the freeze-drier to manufacture a freeze-dried body for a filler.

1 g of the freeze-dried body was mixed with 10 ml of sterilized injection water to manufacture filler injection.

TABLE 2

| | Example 1 | Comparative preparation example 1 | Comparative preparation example 2 |
|---|---|---|---|
| Average particle diameter of PDO microparticle $(D_{50})$ ($\mu$m) | 20~50 | 20~100 | 100.01~200 |

TABLE 2-continued

| | Example 1 | Comparative preparation example 1 | Comparative preparation example 2 |
|---|---|---|---|
| Microparticle & excipient(Carboxymethyl cellulose: CMC) Mixed weight ratio [Microparticle:Excipient] | 95:5 | 95:5 | 85:15 |

Examples 1-1 & 1-2

Except that the content of NaOH was changed to 1 part by weight and 3 parts by weight on the basis of 100 parts by weight of PDO microparticles, a freeze-dried body and filler injection were manufactured according to the same method as in the Example 1.

Examples 1-3 & 1-4

Except that the wet surface treatment was performed for 30 seconds and 5 minutes, respectively, instead of 1 minute, a freeze-dried body and filler injection were manufactured according to the same method as in the Example 1.

Examples 1-5

Except that the mixing weight ratio of the hydrophilic surface-treated polydioxanone microparticles and the CMC was 99:1, instead of 95:5, a freeze-dried body and filler injection were manufactured according to the same method as in the Example 1.

Examples 1-6

Except that the mixing weight ratio of the hydrophilic surface-treated polydioxanone microparticles and the CMC was 97:3, instead of 95:5, a freeze-dried body and filler injection were manufactured according to the same method as in the Example 1.

Examples 1-7

Except that the mixing weight ratio of the hydrophilic surface-treated polydioxanone microparticles and the CMC was 98:2, instead of 95:5, a freeze-dried body and filler injection were manufactured according to the same method as in the Example 1.

Example 2

Stainless steel of a thickness of 1 mm (width of 40 mm and length of 150 mm), and two electrodes were arranged side by side in a plasma reactor of the plasma reaction device of FIG. 5 in a state in which a distance between the two electrodes was 10 mm.

1 g of PDO microparticle manufactured according to the preparation example 1 was put along an inner pipe of the plasma reactor of FIG. 1. In this instance, air was injected at 500 mL/min from the plasma reactor, and alternating current of 400 Hz was applied to the electrodes to which a power supply unit was connected, so that plasma-treated air came into direct contact with the PDO microparticles. After one-minute reaction, biodegradable polymer microparticles were obtained from the plasma reaction device.

Compared with the PDO microparticles which were not surface-treated, the surface-treated PDO microparticles could prevent self-aggregation to improve dispersibility since lots of polar operation groups were induced and hydrophile groups were induced.

When hydrophilic surface-treated polydioxanone microparticles and 1 g of carboxymethyl cellulose CMC (standard viscosity: 2% solution reference, 1125-2100 cc), which was an excipient (biocompatible carrier), were added and dissolved in 100 ml of water so as to manufacture a mixed solution. The mixed weight ration of the hydrophilic surface-treated polydioxanone microparticles and the CMC in the mixed solution is 95:5.

The mixed solution of a predetermined amount was poured into a hemispherical mold having a height of 5 mm, was put into a freezer which had internal temperature of −75° C. to suddenly cool and freeze the mixed solution, and then, was freeze-dried for 24 hours using a freeze-drier to manufacture a freeze-dried body for a filler.

The pre-freeze-dried body was put in the freezer which had internal temperature of −20° C. to freeze-dry the pre-freeze-dried body for 24 hours using the freeze-drier to manufacture a freeze-dried body for a filler.

The freeze-dried body was mixed with sterilized injection water to manufacture filler injection.

The content of the polydioxanone microparticles in the filler injection was 8% by weight, the content of the biocompatible carrier was 1% by weight, and the content of the injection water was 91% by weight.

Example 2-1

Except that the mixing weight ratio of the microparticles and the excipient (Carboxymethyl cellulose) was changed to 99:1, a freeze-dried body and filler injection were manufactured in the same manner as in the Example 2.

Example 2-2

Except that the mixing weight ratio of the microparticles and the excipient (Carboxymethyl cellulose) was changed to 97:3 instead of 95:5, a freeze-dried body and filler injection were manufactured in the same manner as in the Example 2.

Example 2-3

Except that the mixing weight ratio of the microparticles and the excipient (Carboxymethyl cellulose) was changed to 98:2 instead of 95:5, a freeze-dried body and filler injection were manufactured in the same manner as in the Example 2.

Example 3

Except that, instead of the polydioxanone microparticles of the preparation example 1, Poly-L-Lactic acid (PLLA) microparticles of the preparation example 2 were used as the biodegradable polymers, filler injection was manufactured in the same manner as in the Example 1.

Example 4

Except that, instead of the polydioxanone microparticles, Poly-ε-caprolactone (PCL) microparticles of the preparation example 3 were used as the biodegradable polymers, filler injection was manufactured in the same manner as in the Example 1.

Comparative Example 1 (PDO Microparticles which had the Average Particle Diameter ($D_{50}$) of 20 to 100 μm and were Surface-Treated with Acid)

1 g of PDO microparticles manufactured according to the preparation example 1 were put in an aqueous hydrochloric acid solution, which was an acid catalyst, stirred at 200 rpm, and then, surface-treated for 1 minute to obtain surface-treated PDO-microparticles. Except that the PDO fume microparticles were used, a freeze-dried body and filler injection were manufactured in the same manner as in the Example 1.

Comparative Example 2 (Using PDO Microparticles of Comparative Preparation Example 1 without Hydrophilic Surface Treatment)

Except that the PDO microparticles of the comparative preparation example 1 having the average particle diameter of 20 to 100 μm were used, a freeze-dried body and filler injection were manufactured in the same manner as in the Example 1.

Comparative Example 3 (Using PDO Microparticles of Comparative Preparation Example 2 without Hydrophilic Surface Treatment)

Except that the PDO microparticles of the comparative preparation example 2 having the average particle diameter of 100.1 to 200 μm were used, a freeze-dried body and filler injection were manufactured in the same manner as in the Example 1.

Comparative Example 4

Except that the PLLA microparticles of the preparation example 2 were used, a freeze-dried body and filler injection were manufactured in the same manner as in the Example 1.

Comparative Example 5

Except that the PCL microparticles of the preparation example 3 were used, a freeze-dried body and filler injection were manufactured in the same manner as in the Example 1.

Comparative Example 6 (Using PDO Microparticles without Surface Treatment)

Except that the PDO microparticles having the average particle diameter of 20 to 50 μm obtained according to the preparation example 1 and carboxymethyl cellulose (CMC), which was an excipient, were mixed at a mixed weight ratio of 98:2, a freeze-dried body and filler injection were manufactured in the same manner as in the Example 1.

Comparative Example 7

Except that the microparticles having the average particle diameter of 20 to 50 μm obtained according to the preparation example 1 and carboxymethyl cellulose (CMC), which was an excipient, were mixed at a mixed weight ratio of 80:20, a freeze-dried body and filler injection were manufactured in the same manner as in the Example 1.

Evaluation Example 1: Evaluation of
Hydrophilicity by Surface Treatment Method

In order to confirm a hydrophilicity increase effect of surface treatment of the biodegradable polymer microparticle for a filler, a powder-water contact angle was measured by the following method.

For the hydrophilic evaluation, a glass tube having an inner diameter of 1.2 cm was filled with 10 g of PDO microparticles, and was erected on the floor filled with sufficient water in a contact angle measuring apparatus.

After that, after waiting until the water drawn by the capillary force was raised no longer, the water level in the tube and a radius of a meniscus were measured so as to obtain a water contact angle based on the measured value.

After that, through the contact angle measuring apparatus, results before/after treatment are shown in the following Table 3.

TABLE 3

| Division | Surface treatment method | Contact angle before surface treatment (°) | Contact angle after surface treatment (°) |
|---|---|---|---|
| Example 1 | NaOH aqueous | 65 | 35.7 |
| Example 1-5 | solution | | 35.5 |
| Example 1-6 | | | 35.7 |
| Example 1-7 | | | 35.6 |
| Example 2 | Plasma | | 35.2 |
| Example 2-1 | | | 35.1 |
| Example 2-2 | | | 35.2 |
| Example 2-3 | | | 35.2 |

Referring to Table 3, according to the examples 1, 1-5, 1-6, 1-7, 2, 2-1, 2-2, and 2-3, the contact angle was lower than before the surface treatment. Therefore, it was confirmed that the hydrophilic surface was well formed on the surface of the biodegradable polymer particle.

Evaluation Example 2: Evaluation of Precipitation by Size Distribution of PDO Microparticles 1 g of the freeze-dried bodies obtained in the examples 1 to 5, examples 1 to 6, examples 1 to 7, example 2, example 2-1, example 2-2, examples 2-3, and comparative examples 1 to 7 were placed in a vial containing 10 ml of water, and vortexing was applied for one minute so as to make a dispersion state. Thereafter, it was left for 60 minutes in order to confirm whether the microparticles have been precipitated. The results of the precipitation evaluation of the freeze-dried bodies obtained according to the example 1, comparative example 1 and comparative example 2 are shown in FIG. 1, and the results of the precipitation evaluation using the freeze-dried bodies obtained in the example 2, comparative example 3 and comparative example 6 are shown in FIG. 2.

Referring to FIG. 1, the freeze-dried bodies of the comparative examples 1 and 2 were all precipitated when 15 minutes had passed, but a precipitation phenomenon of the freeze-dried body of the example 1 was observed after 60 60 minutes. As illustrated in FIG. 2, the freeze-dried body of the example 1 showed the precipitation phenomenon after 60 minutes like the freeze-dried body of the example 1. However, the freeze-dried body of the comparative example 3 was completely precipitated after 15 minutes.

In addition, precipitation states using the hydrophilic surface-treated freeze-dried bodies obtained according to the examples 1, 2, 2-1, and 2-2 and the comparative examples 1-6 were confirmed, and the results are shown in Table 4.

TABLE 4

| Surface treatment method | Precipitation time(minute) |
|---|---|
| Example 1 | 60 |
| Example 1-5 | 60 |
| Example 1-6 | 60 |
| Example 1-7 | 60 |
| Example 2 | 60 |
| Example 2-1 | 60 |
| Example 2-2 | 60 |
| Example 2-3 | 60 |
| Comparative example 1 | 15 |
| Comparative example 2 | 15 |
| Comparative example 3 | 15 |
| Comparative example 4 | 15 |
| Comparative example 5 | 15 |
| Comparative example 6 | 15 |

Moreover, also in the comparative examples 1 to 6, it was confirmed that the freeze-dried bodies were all precipitated when 15 minutes had passed.

In the examples 1, 1-5, 1-6, 1-7, 2, 2-1, 2-2, and 2-3, the PDO particles in the freeze-dried bodies were maintained in a very stable dispersion state for 60 minutes in a size range of 20 to 50 μm.

Furthermore, evaluation was performed in the same manner as the evaluation method in relation to precipitation in the filler injections of the examples 5 and 6. As a result, it was confirmed that a stable dispersion state was shown like the filler injection of the example 1.

Meanwhile, in the case of the comparative example 7, the dispersion state could be stably maintained due to the high content of the excipient. However, as described in the following Evaluation example 4, because the injection containing the excipient increased the injection force by increasing the viscosity of the injection and the relative content of the PDO particles was reduced, the volume was reduced after 4 weeks, and thus the degree of satisfaction of the treatment was reduced.

Evaluation Example 3: Characteristics of Average
Particle Diameter and Particle Distribution The average particle diameters ($D_{50}$), ($D_{10}$), and ($D_{90}$) and the particle size distribution before sorting of the PDO particles manufactured according to the preparation example 1 were measured by using a laser diffraction scattering type particle size analyzer (PSA).

The average particle diameters and particle distribution characteristics were described in the following Table 5.

TABLE 5

| Division | $D_{50}$ | $D_{10}$ | $D_{90}$ |
|---|---|---|---|
| Preparation example 1 | 50 | 15 | 65 |

The full width at half maximum (FWHM) in the particle size distribution of the polymer microparticle manufactured according to the preparation example 1 was less than 50 μm.

Evaluation Example 4: Viscosity

Viscosity of the filler injections according to the example 1 and the comparative example 7 were measured and described in the following Table 6.

TABLE 6

| Division | Viscosity |
|---|---|
| Example 1 | 50 cP |
| Comparative example 7 | 5,000 cP |

As shown in Table 6, it was shown that the injection of the example 1 was reduced in viscosity compared to the injection of the comparative example 7. The injection of the example 1 having the above-mentioned viscosity was easy to be injected due to low injection force, had a relatively high content of the PDO microparticles and maintained the volume for a long time since not containing the excipient, thereby improving the degree of satisfaction of the treatment.

Evaluation Example 5

The filler injections of the example 1 and the comparative example 6 were respectively charged into syringes, and 200 μl of the injection was injected into a hair-less mouse. The size of the injected part was measured for four weeks, and a change in size was continuously measured at a cycle of a predetermined period, and the results are shown in Table 7.

TABLE 7

| Division | Volume(%) immediately after treatment | Volume(%) after one week | Volume(%) after four weeks |
|---|---|---|---|
| Example 1 | 100 | 90 | 100 |
| Comparative example 7 | 100 | 10 | 75 |

As shown in Table 7, it was confirmed that the injection of the example 1 was significantly reduced in initial volume compared to that of the comparative example 7.

While the present disclosure has been described with reference to the accompanying drawings, it will be understood by those skilled in the art that the present disclosure can be practiced in other specific forms without changing the technical idea or essential features thereof. Therefore, it is to be understood that the embodiments described above are illustrative and not limiting in all respects.

The invention claimed is:

1. A manufacturing method of a freeze-dried body for a filler, the manufacturing method comprising:

preparing a biodegradable polymer microparticle for a filler having an average particle diameter of 20-50 μm, wherein the biodegradable polymer microparticle is a polydioxanone microparticle;

surface-treating the biodegradable polymer microparticle with plasma using discharge or base to manufacture a surface-treated biodegradable polymer microparticle, wherein the surface-treated biodegradable polymer microparticle is a polydioxanone microparticle which has a carboxyl group on a surface thereof;

dissolving the surface-treated biodegradable polymer microparticle, a biocompatible carrier, and distilled water to obtain a mixed solution; and freeze-drying the mixed solution to obtain a freeze-dried body, wherein the surface-treating with plasma using discharge comprises:

fluidizing the biodegradable polymer microparticle through an inner pipe within a plasma reaction device, injecting 400 to 600 mL/min of air into the inner pipe through a gas supply unit in the plasma reaction device, and directly applying 300 Hz to 500 Hz of alternating current to an electrode to which a power supply unit is directly connected so that plasma-treated air is fluidized together with and comes into contact with the biodegradable polymer microparticle, and wherein the surface-treating with base is performed through adding and treating the biodegradable polymer microparticle to 0.1 to 5% by weight of a sodium hydroxide solution to obtain microparticles, and washing and vacuum-drying the microparticles, wherein a content of sodium hydroxide is 0.1 to 5 parts by weight based on 100 parts by weight of the biodegradable polymer microparticles.

2. The manufacturing method according to claim 1, wherein the biodegradable polymer microparticle is manufactured through: providing a first composition containing organic solvent miscible with water, and polydioxanone; providing a second composition containing surfactant and water; preparing mixture by mixing the first composition and the second composition; stirring the mixture to prepare a third composition containing polymer microparticles; separating the polymer microparticles from the third composition; and sorting polymer microparticles, of which the average particle diameter is 20 to 50 μm, from the separated polymer microparticles.

3. The manufacturing method according to claim 2, wherein the first composition is free of surfactant, and the second composition contains surfactant.

4. The manufacturing method according to claim 2, wherein the organic solvent contained in the first composition is completely or partially mixed with water and does not form a separate phase differentiated from water.

5. The manufacturing method according to claim 1, wherein the surface-treated biodegradable polymer microparticle has an average particle diameter (D50) of 20 to 50 μm, wherein the surface-treated biodegradable polymer microparticle is a plasma surface-treated product or a base surface-treated product using discharge of the biodegradable polymer microparticle, wherein a content of the biocompatible carrier is 1 to 5 parts by weight based on 100 parts by weight of the freeze-dried body, wherein the biocompatible carrier is sodium carboxymethyl cellulose, and a moisture content in the freeze-dried body is 0.5 to 1.0% by weight, wherein a powder-water contact angle value to the surface-treated biodegradable polymer microparticle is 35.1 to 35.7°, wherein the base surface-treated product of the biodegradable polymer microparticle is a product obtained through: adding 0.1 to 5% by weight of a sodium hydroxide solution to the biodegradable polymer microparticle for a filler, and stirring it for 30 seconds to 300 seconds; and washing and vacuum-drying the product obtained through the stirring, wherein the content of sodium hydroxide is 1 to 5 parts by weight based on 100 parts by weight of the biodegradable polymer microparticle for a filler, and wherein the plasma surface-treated product is a product obtained through: applying voltage to the biodegradable polymer microparticle for a filler to induce discharge; and performing a discharge treatment of the biodegradable polymer microparticle, wherein the discharge treatment of the biodegradable polymer microparticle comprises:

fluidizing the biodegradable polymer microparticle through an inner pipe within a plasma reaction device, injecting 400 to 600 mL/min of air into the inner pipe through a gas supply unit in the plasma reaction device;

directly applying 300 Hz to 500 Hz of alternating current to an electrode to which a power supply unit is directly connected to obtain plasma-treated air; and making the plasma-treated air fluidized together with and come into contact with the biodegradable polymer microparticle.

6. The manufacturing method according to claim 1, wherein a 10% cumulative diameter (D10) of the surface-treated biodegradable polymer microparticle is 10 to 20 μm, and a 90% cumulative diameter (D90) of the surface-treated biodegradable polymer microparticle is 60 to 70 μm.

7. The manufacturing method according to claim 6, wherein the surface-treated biodegradable polymer microparticle satisfies Formula 1 in connection with the 10% cumulative diameter (D10), the average particle diameter (D50), and the 90% cumulative diameter (D90), $$0.8 \leq (D_{90} - D_{10})/D_{50} \leq 3.5 \qquad \text{[Formula 1]}$$

8. The manufacturing method according to claim 1, wherein the number average molecular weight (Mn) of the biodegradable polymer microparticle is 50,000 to 500,000 Daltons.

\* \* \* \* \*